US00PP30732P3

(12) United States Plant Patent
Maillard et al.

(10) Patent No.: US PP30,732 P3
(45) Date of Patent: Jul. 23, 2019

(54) PEACH TREE NAMED 'CRISPLOVA'

(50) Latin Name: ***Prunus persica* (L.) Batsch**
Varietal Denomination: CRISPLOVA

(71) Applicant: AGRO SELECTIONS FRUITS, Elne (FR)

(72) Inventors: Arsene Maillard, Elne (FR); Laurence Maillard, Elne (FR)

(73) Assignee: AGRO SELECTIONS FRUITS, Elne (FR)

( * ) Notice: Subject to any disclaimer, the term of this patent is extended or adjusted under 35 U.S.C. 154(b) by 0 days.

(21) Appl. No.: 15/732,469

(22) Filed: Nov. 17, 2017

(65) Prior Publication Data

US 2018/0153073 P1 May 31, 2018

(30) Foreign Application Priority Data

Nov. 25, 2016 (QZ) ..... PBR 2016/2955

(51) Int. Cl.
*A01H 5/08* (2018.01)
*A01H 6/74* (2018.01)

(52) U.S. Cl.
USPC ..... Plt./197
CPC ..... *A01H 6/7463* (2018.05); *A01H 5/08* (2013.01)

(58) Field of Classification Search
USPC ..... Plt./156, 180, 194, 197
See application file for complete search history.

*Primary Examiner* — Susan McCormick Ewoldt
*Assistant Examiner* — Karen M Redden
(74) *Attorney, Agent, or Firm* — Westerman, Hattori, Daniels & Adrian, LLP

(57) ABSTRACT

A new and distinct variety of yellow peach tree denominated 'CRISPLOVA' that has fruits with high eating quality and very long shelf life without alteration before and after harvesting, with a semi-sweet orange yellow flesh, with a red pigmentation into and around the stone cavity, the pigmentation having a star shape, and an attractive luminous and homogenous skin with a very high percentage of purple red blush on skin surface, on an orange red background.

3 Drawing Sheets

Botanical classification: *Prunus persica* (L.) Batsch.
Variety denomination: 'CRISPLOVA'.

This application claims priority of Community plant variety right No. 2016/2955 filed on Nov. 25, 2016 (Nov. 25, 2016) which is hereby incorporated by reference in its entirety.

BACKGROUND OF THE NEW VARIETY

The present invention relates to a new and distinct variety of yellow peach tree, *Prunus persica* (L.) Batsch, which has been given the variety denomination 'CRISPLOVA'. The new variety named 'CRISPLOVA' is also known as 8C.01.277.14 PJ or ASF1444. Indeed, before giving a name to a new and distinct variety of fruit tree, a provisional reference is assigned, considering the references of a tree in orchard. This provisional reference is constituted firstly with the number of the parcel on which the tree has grown, then the number of the line, the tree number and finally the year of selection. Then before being named 'CRISPLOVA', the provisional reference of this peach tree variety was 8C.01.277.14, corresponding to the tree 277 located in line 01 of the parcel 8C and selected during the year 2014. The letters "PJ" are related to the first letters of the type of tree in French (PJ for Pêche Jaune, that means "yellow peach"). Once the hybrid selected, the breeder assigned a clone reference that begins with the letters "ASF" followed by the year of selection and a number corresponding to the maturity order. The final name is only assigned once the application has been filed and the name approved after its publication in the official bulletin. For the variety 'CRISPLOVA', the clone reference was 'ASF1444'.

This new tree 'CRIPSLOVA' produces fruits with a long shelf life without alteration both on the tree after growth completion and after harvesting, very good eating quality, clingstone orange yellow flesh fruits with a red pigmentation, for fresh market in August in the Pyrénées-Orientales department, France.

ORIGIN OF THE VARIETY

The 'CRISPLOVA' yellow peach tree originated from a cultivated area of the south of France, in the Pyrénées-Orientales department, where it was tested.

This place is under a Mediterranean climate (a temperate area), on the Mediterranean coastline. Winters are gentle and summers warm and dry. The amount of days with temperatures below 7° Celsius can vary between 600 and 1200 hours per year. The place is sunny, with 2400 to 2800 hours of sunny days per year on average. The prevailing wind is called 'Tramontane': it dries the air, clears the sky from clouds, but its intensity can be strong and affect the harvest, fruit quantity and/or quality. Marine moisture does not affect the place. Precipitations are irregular through the year and from one year to another. The amount of rainy days does not exceed 80 days per year, and are mostly found in Spring and Autumn. In May and October, very intense precipitations occasionally happen. Summer is dry with a few thunderstorms.

The 'CRISPLOVA' variety resulted from an open pollination of the 'SWEETEMBER' white peach tree (U.S. Plant Pat. No. 28,506) which was used as the seed parent. Thus, the pollen parent is unknown.

The 'CRISPLOVA' variety was obtained by hybridizing and propagated by grafting on a 'INRA® GF677' (not patented) rootstock trees. It has been determined to have unique tree and fruit characteristics making it worthy for commercial fresh fruit production. There are no known effects of the standard rootstock trees set forth above on the scion cultivar. Asexually propagated plants remained true to the original tree and all characteristics of the tree and the fruit were transmitted. The plant was reproduced asexually by us in Les Régalines, Route d'Alenya, La Prade de Mousseillous, 66200 ELNE, Pyrénées-Orientales, France. More particularly, the plant was reproduced by grafting.

SUMMARY OF THE VARIETY

The new and distinct variety 'CRISPLOVA' yellow peach tree blooms generally during the March near Elne in the Pyrénées-Orientales department, France. More particularly, the beginning of the blooming period occurs between February 28$^{th}$ and March 16$^{th}$. The blooming period is considered medium. However, it was observed that its early date of blooming seems to be highly dependant on climatic conditions.

The first fruit of 'CRISPLOVA' ripens generally during August. More particularly, the beginning of the ripening period occurs between August 2$^{nd}$ and August 27$^{th}$. However, it was observed that its early date of maturity seems to be highly dependant on climatic conditions.

DESCRIPTION OF THE DRAWINGS

In the accompanying drawing, which are as nearly true as it is reasonably possible to make in a color illustration of this type.

Figure 1:
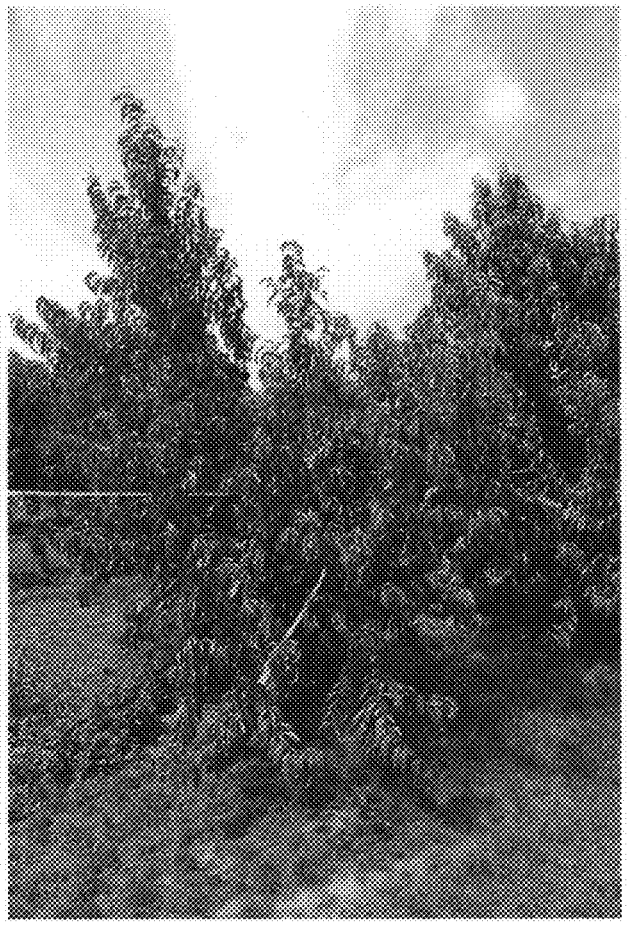
FIG. 1 is a color photograph which shows a view of a tree of the new variety in orchard.
Figure 2:
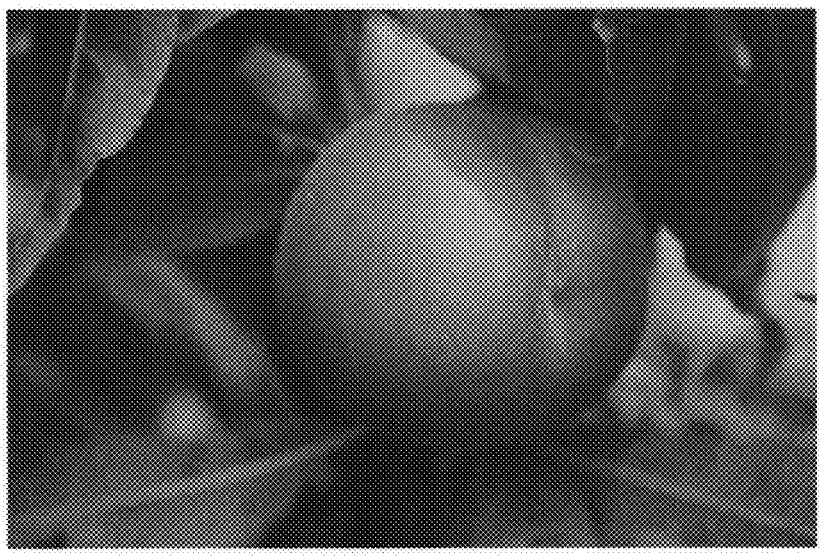
FIG. 2 is a color photograph that shows a close view of a typical specimen of the fruit of the new variety 'CRISPLOVA' on the tree.
Figure 3:
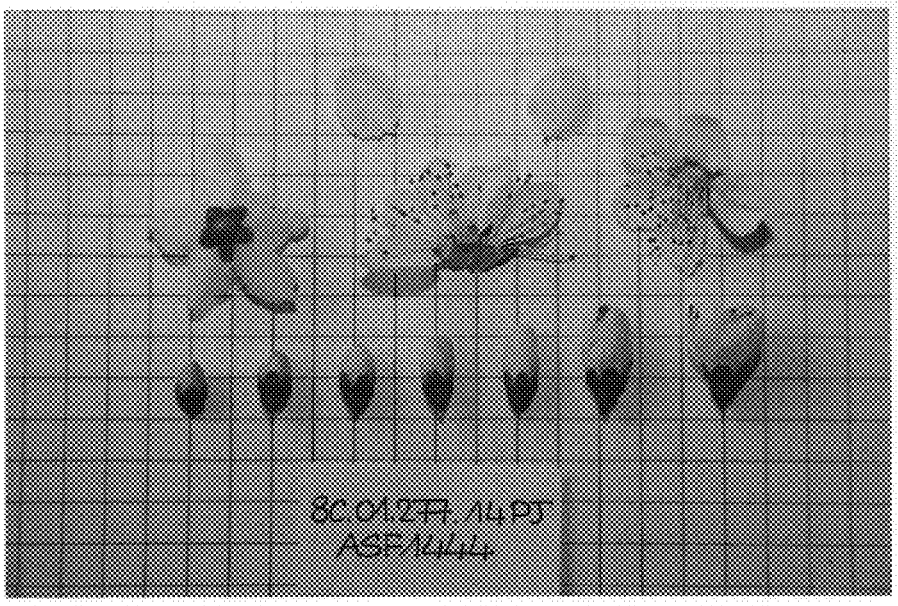
FIG. 3 is a color photograph which depicts the flower buds at different development stages, and the reverse and side view of the flower and the reproductive organs with petals removed, of the new variety.
Figure 4:
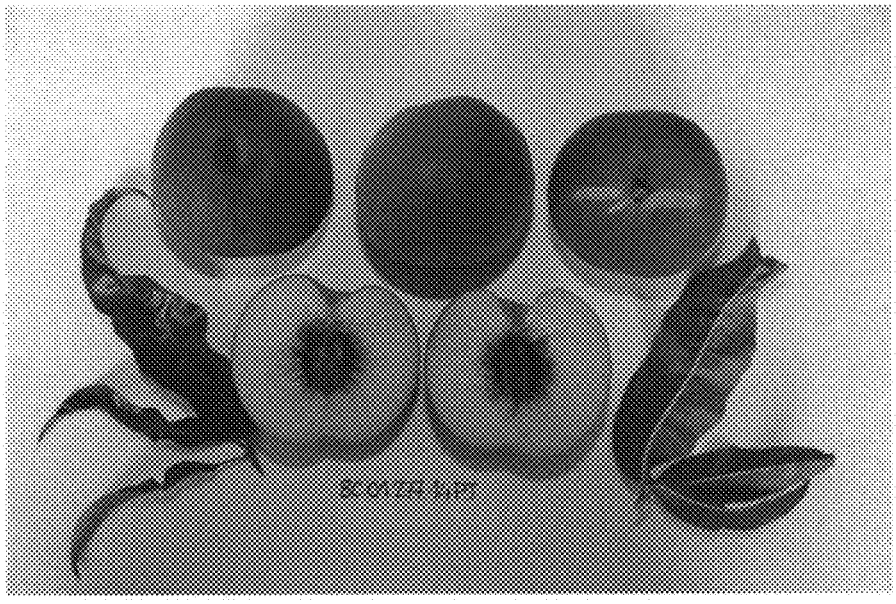
FIG. 4 is a color photograph which shows four specimens of the fruit, one having been cut in half with the pit being left in one of the halves for depicting leaves, fruit flesh, pit and pit cavity of the new variety
Figure 5:
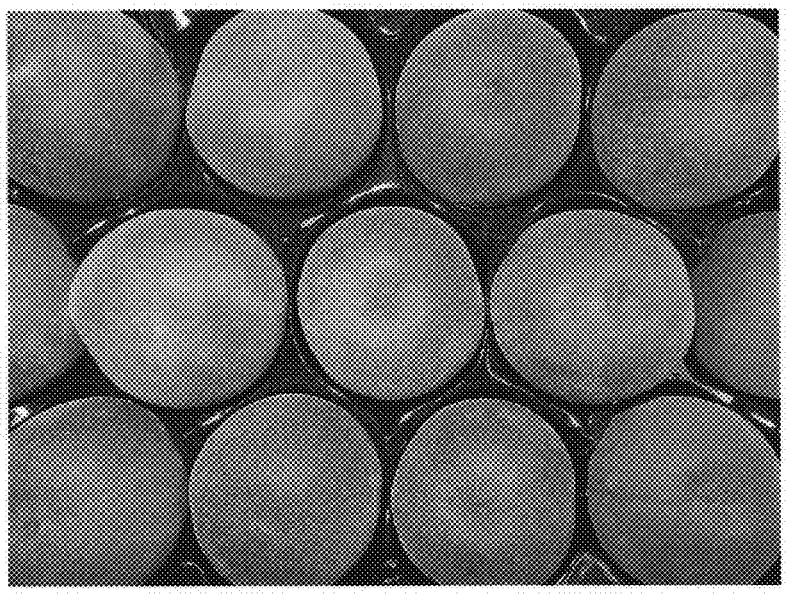
FIG. 5 is a color photograph that shows a close view of typical specimens of the fruit of the new variety 'CRISPLOVA' at ripening time.
Figure 6:
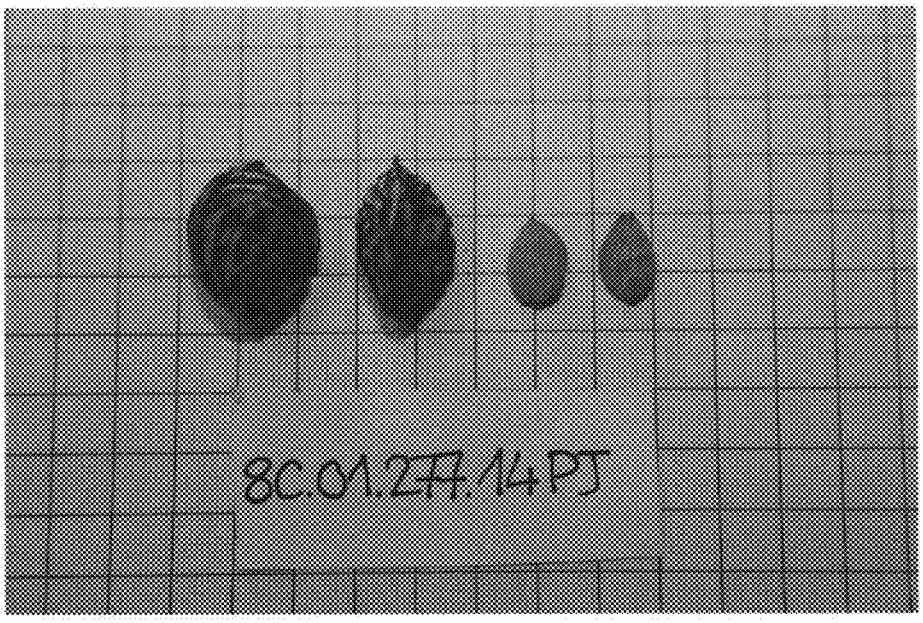
FIG. 6 is a color photograph that shows different views of the stone of the new variety and the kernel of the stone.

Due to chemical development, processing and printing, the flowers, stones and fruits depicted in these photographs may or may not be accurate when compared to the actual botanical specimen.

DETAILED BOTANICAL DESCRIPTION

The tree, flowers, and fruit may vary in slight detail due to variations in soil type, cultural practices, and climatic condition. The potential for commercial production of fresh fruits by 'CRISPLOVA' is high, due to fruit very long shelf life without alteration after harvesting.

Trees are vigorous and large stature half-standing in a semi-flared out aspect. The anthocyanic coloration of flowering shoot is present excluding brushwood side away from sun. The time of beginning of flowering is considered medium; flowering begins at the end of February or during March. The type of flower is showy (rosette) with large petal size. Petals are very pale or pale pink. Leaf glands are present and round. The fruit flesh orange yellow generally with a red pigmentation into and around the stone cavity. The fruit skin is thick, with a luminous and homogenous red purple blush on an orange red background. The stone is clingstone and its size is medium to small. Fruit taste is semi-sweet, very aromatic and with a high level of sugars.

Compared to 'CRISPDELICE SUN' peach variety (U.S. Plant Pat. No. 19,231), 'CRISPLOVA' variety has a later period of maturity. The amount of flowers produced by the new variety 'CRISPLOVA' is more intense than for the 'CRISPDELICE SUN' variety. More particularly, the amount of flowers produced by the variety 'CRISPLOVA' is between 45 and 50 flowers per linear meter whereas between 30 and 40 flowers per linear meter for the known 'CRISPDELICE SUN' variety.

Compared to 'JULIEPRETTY' yellow peach variety (U.S. Plant Pat. No. 20,611), the new variety 'CRISPLOVA' has a similar period of maturity. The flavour of the 'JULIEPRETTY' fruits is considered balanced whereas the flavour of the flesh fruit of the new variety is semi-sweet.

Compared to the seed parent 'SWEETEMBER' (U.S. Plant Pat. No. 28,506), the new variety 'CRISPLOVA' is a yellow peach whereas 'SWEETEMBER' is a white peach variety. Moreover the new variety 'CRISPLOVA' has an earlier period of maturity than 'SWEETEMBER'. In particular the fruit of 'CRISPLOVA' ripens generally during August whereas those of 'SWEETEMBER' ripen generally during September.

DETAILED DESCRIPTION

Referring more specifically to the pomological details of this new and distinct variety of yellow peach tree, the following was observed on trees in their third growing season (second year of production). The characteristics were observed under the ecological conditions prevailing at the orchards located near the town of Elne, Pyrénées-Orientales departement, France. All observations have been done on rootstock cultivars. Used rootstocks were "INRA® GF677" trees. All major color code designations are by reference to The R.H.S. Colour Chart (Fourth Edition) provided by The Royal Horticultural Society of Great Britain.

Tree:

*Size.*—

*Generally.*—Considered large. The tree size the first year was approximately 200 to 280 cm. The tree was pruned during each following dormant season to a height of approximately 250 cm. Current season shoots growth could reach 80 cm. The tree size from the second year (second and next years) reached a final height of 330 cm including current season shoots length. The tree size is consistently reduces to 250 cm the next years.

*Spread.*—Approximately 100 cm with a cylindrical shape. The whole orchard was oriented to a central leader organization, with tree lines spaced of 4.0 meters and trees spaced of 1.0 meter in a same tree line. As a result, tree spread was about 100 cm and the orchard contained 2500 trees by hectare.

*Vigor*.—Considered medium.

*Productivity*.—The productivity is good to very good and regular, every year. Fruit set is spaced by thinning to develop the remaining fruit into the desired market sized fruit. The number of the fruit set varies with the prevailing climatic conditions and cultural practices employed during the bloom period and is therefore not distinctive of the present variety. The productivity is between 45 to 50 metric tons per hectare.

*Bearer*.—Very regular. The fruit distribution is considered homogenous on mixed branches and spurs having more than 1 year. Thinning should be reduced or very reduced because of the capacity of the tree to produce homogeneous fruits with a high potential.

*Form*.—The 'CRISPLOVA' variety has naturally a semi-flared shape.

*Density*.—Considered dense.

*Hardiness*.—The present tree was grown and evaluated in France. The variety appears to be hardy under the central Pyrénées-Orientales departement typical climatic conditions. Experimentations on different sites with winter chilling requirement comprised between 350 hours and 1200 hours showed a good behaviour of the tree in all cases. No damages were caused by ascertained temperatures as low as −12 degrees Celsius in winter. The tree was also very resistant to frosty springtime weather.

Trunk:

*Diameter*.—Approximately 5.4 centimeters in diameter when measured at a distance of approximately 20 centimeters above the soil level.

*Bark texture*.—Considered rough, with lenticels.

*Lenticels*.—Numerous lenticels are present. The number of lenticels reaches 5 lenticels per $cm^2$. The lenticels range in size from approximately 3.0 millimeters in width, and about 1.0 millimeter in height.

*Lenticel color*.—The lenticels have a beige to light orange color (RHS Greyed Yellow 161 A or RHS Greyed Orange 163 C).

*Bark coloration*.—The bark has a silver to brown color (RHS Grey 201 A to RHS Grey 201 B) darker than the lenticel color.

Branches:

*Size*.—The branches are pruned to approximately 1.0 meter in length.

*Diameter*.—Average as compared to other peach varieties. The current season shoots have a diameter from 4.0 to 5.0 millimeters, and mature branches have a diameter from 9.0 to 10.0 millimeters.

*Surface texture*.—Smooth for current season shoots and rough, with lenticels, for mature branches, wood which is several years old has no furrowed appearance.

*Crotch angles*.—Primary branches are considered variable, but the crotch angles are generally of 50 degrees from the horizontal axis. This particular characteristic is not considered distinctive of the variety, however.

*Current season shoots*.—

*Internode length*.—Generally 18.0 to 20.0 millimeters.

*Color*.—The color of new shoot tips is considered green (RHS Yellow Green 144 A) on lower part of new shoot tips, whereas the upper part is darker and colored in brown to purple red (RHS Greyed Purple N 186 C), depending on the level on the tip.

*Mature branches*.—

*Internode length*.—Generally from 27.0 to 31.0 millimeters.

*Color of mature branches*.—Grey to brown (RHS Brown N 200 B).

*Lenticels*.—Numerous lenticels are present on mature branches. The number of lenticels reaches 4 lenticels per $cm^2$. The size of lenticels is considered small. The lenticels range in size from approximately 1.50 to 1.80 millimeters in width, and from 1.0 to 1.20 millimeters in height. The lenticel shape is round and slightly stretched.

*Lenticel color*.—The lenticels on mature branches have a light beige color (RHS Greyed Orange 164 D).

Leaves:

*Size*.—Considered medium for the species. The ratio leaf length/leaf width is 3.57 millimeters.

*Leaf length*.—Approximately 144.0 to 152.0 millimeters without leaf petiole. The medium length is about 147.8 millimeters.

*Leaf width*.—Approximately 39.0 to 44.0 millimeters. The medium width is 41.4 millimeters.

*Leaf base shape*.—Concave.

*Leaf form*.—Lanceolate.

*Leaf tip form*.—Acuminate.

*Leaf color*.—

*Upper leaf surface*.—Yellow green (RHS Yellow Green 147 A).

*Lower surface*.—A lighter green (RHS Yellow Green 146 A) than the upper leaf surface color.

*Leaf texture*.—Smooth and glabrous on both upper and lower surfaces of the leaf.

*Leaf venation*.—Pinnately veined.

*Mid-vein*.—

*Color*.—Light green, almost cream white (RHS Yellow Green 151 D). The color may evolve with maturity.

*Leaf margins*.—Slightly undulating.

*Form*.—Considered slightly dentate.

*Uniformity*.—Leaves are isolated or grouped by 2 or 3. In this last case, one leaf of normal size is found with one or two smaller leaves (at least 50% smaller).

*Leaf petioles*.—

*Size*.—Considered medium.

*Length*.—About 10.0 to about 13.0 millimeters.

*Diameter*.—About 2.0 millimeters.

*Petioles color*.—

*Upper petiole surface*.—Light green (RHS Yellow Green 144 A).

*Lower surface*.—Light green (RHS Yellow Green 144 C).

*Leaf glands*.—

*Size*.—Considered small. Their size is about 1.0 millimeter in length and in width.

*Number*.—Generally 2 glands per leaf.

*Type*.—Round.

*Color*.—On young leaves, leaf glands color is considered a light green (RHS Green 145 B). On older leaves, leaf glands color turns to a dark brown (RHS Grey Brown 199 A to RHS Grey Brown 199 B).

*Margins*.—Smooth and regular.

*Leaf stipules*.—

*Generally*.—No leaf stipules were observed. But as seen in the characteristic relative to the leaves uniformity, it is possible to find leaves by groups of 2 or 3, with a normal-size leaf and smaller ones.

Flowers:

*Flower buds.*—

*Generally.*—At pre-floral stage of development, the floral buds are conic in form with a round tip. Their form is evolving until blooming, with variable dimensions. Just before blooming, floral buds are approximately 8.0 to 10.0 millimeters wide and approximately 15.0 to 20.0 millimeters long.

*Color.*—This characteristic is dependent upon the proximity to bloom. At pre-floral stage of development (stage A), the bottom of the flowers buds, formed by the sepals, is of purple-brown color (RHS Greyed Purple 183 A) on their outer surface, and green (RHS Yellow green 146 B or RHS Yellow Green 146 C) on their inner surface. The margins of the sepals are slightly greenish (RHS Yellow Green 152 A). The corolla, formed by the petals, is generally of pale pink color (RHS Red Purple 69 A or RHS Red Purple 69 B or RHS Red Purple 69 C or RHS Red Purple 69 D) on both faces. Petals color shows an evolution until the end of flowering.

*Hardiness.*—The buds are considered hardy under typical central Pyrénées-Orientales departement climatic conditions. No winter injury was noted during the last several years of evaluation in the central Pyrénées-Orientales departement, with winter temperatures as low as −10 degrees Celsius in January. The current variety has not been intentionally subjected to drought or heat stress, but the variety showed a very good resistance in orchard to temperatures up to 42 degrees Celsius with an average temperature between 28 and 30 degrees Celsius during 3 weeks in summer.

*Date of bloom.*—The blooming time generally begins at the end of February or during march. The first bloom was observed on 2015.

*Blooming time.*—Considered medium in relative comparison to other commercial peach cultivars grown in the Pyrénées-Orientales departement, France. The date of full bloom is observed generally at the middle of the blooming period. The date of bloom varies slightly with climatic conditions and cultural practices. Thus the full bloom was observed from March $16^{th}$ until Mar. 26, 2015, then from February $28^{th}$ until Mar. 8, 2016 then from February $28^{th}$ until Mar. 11, 2017.

*Duration of bloom.*—Approximately 10 to 12 days. This characteristic varies slightly with the prevailing climatic conditions.

*Flower type.*—The variety is considered to have a showy type flower.

*Flower size.*—Considered large. Flower diameter at full bloom is approximately 40.0 to 50.0 millimeters.

*Bloom quantity.*—Considered very abundant, approximately between 35 and 50 flowers per meter, with a good distribution and a high rate of fruit set.

*Flower bud frequency.*—Generally 2 flower buds appear per node, occasionally 1.

*Petal size.*—

*Generally.*—Considered large to very large.

*Length.*—Generally 20.0 to 25.0 millimeters.

*Width.*—Generally 17.0 to 22.0 millimeters.

*Petal form.*—Round-shaped.

*Petal count.*—Generally 5.

*Petal texture.*—Smooth and soft on both upper and lower surfaces of the petal.

*Petal color.*—At the stage F2, when the flower is fully open, both surfaces of the petal are colored with a pale pink color (RHS Red Purple 69 B or RHS Red Purple 69 C or RHS Red Purple 69 D) on both faces when young, becoming slightly darker until the end of blooming.

*Fragrance.*—Sweet to medium.

*Petal claw.*—

*Form.*—The claw is considered to have a narrow form.

*Color.*—Generally the same color as the petal color, a pale pink (RHS Red Purple 69 C or RHS Red Purple 69 D) and sometimes a darker pink than the petal color (RHS Red Purple 61 B).

*Length.*—Approximately 2.0 to 3.0 millimeters.

*Width.*—Approximately 1.0 to 1.5 millimeters.

*Petal margins.*—Generally considered smooth to moderately wavy, sinuate at their base.

*Petal apex.*—

*Generally.*—The petal apices are wide-dome shaped.

*Flower pedicel.*—

*Length.*—Considered medium and having an average length of approximately 2.0 to 3.0 millimeters.

*Diameter.*—Considered average, approximately 1.0 to 2.0 millimeters.

*Color.*—Yellow Green (RHS Yellow Green 145 A or RHS Yellow Green 145 B).

*Calyx.*—

*Internal surface texture.*—Smooth and glabrous.

*Color.*—At the stage F of blooming, when the flower is open, the inner surface of the calyx, namely the flower receptacle, is matt and considered golden-orange (RHS Orange 28 A). The outer surface of the calyx is considered of purple-brown color (RHS Greyed Purple 183 A).

*Sepals.*—

*Sepal count.*—5.

*Surface texture.*—The outer surface has a fine pubescent texture. The inner surface has a smooth texture.

*Margins.*—Smooth

*Size.*—Medium to large.

*Form.*—Conic with a round tip.

*Length.*—Approximately 5.0 to 6.0 millimeters.

*Width.*—Approximately 4.0 to 6.0 millimeters.

*Color.*—At pre-floral stage of development (stage A) the sepals are colored in purple-brown color (RHS Greyed Purple 183 A) on their outer surface, and green (RHS Yellow green 146 B or RHS Yellow Green 146 C) on their inner surface. The margins of the sepals are slightly greenish (RHS Yellow Green 152 A). At the stage F of blooming, the inner surface of the sepals is matt and considered golden-orange (RHS Orange 28 A). The outer surface of the sepals is considered of purple-brown color (RHS Greyed Purple 183 A).

*Average number of stamens per flower.*—Approximately 36 to 42 stamens per flower.

*Anthers.*—

*Color.*—At an early stage of maturity, anthers are colored with an orange yellow color (RHS Yellow Orange 16 A to RHS Yellow Orange 16 B). The color may evolve with maturity to turn in a red or red orange color (RHS Red Group N34 A or RHS Greyed Red Group 178 A).

*Size*.—Medium to large in length, approximately 0.8 millimeter.

*Shape*.—Reniform.

*Pollen production*.—Pollen is abundant, and has a yellow color (Approximately RHS Yellow 12A or RHS Yellow Orange 17 B to RHS Yellow Orange 17 C) which may evolve with maturity. The present variety is considered auto-fertile (self-pollinating).

*Filaments*.—

*Size*.—Medium length, between 12.0 and 21.0 millimeters in length. Filaments length is generally higher than the pistil's length, or equal to the pistil's length.

*Color*.—Considered white (RHS White 155 D) or pale pink (RHS Red Purple 62 C to Red Purple 62 D) to a darker pink (RHS Red Purple 65 C or RHS Red Purple 73 A to RHS Red Purple 73 B) at the end of blooming. The color becomes darker during the blooming.

*Pistil*.—

*Number*.—Usually 1.

*Generally*.—Average in size.

*Length*.—Approximately 18.0 to 20.0 millimeters including the ovary. Pistil's length is generally smaller than the filament's length, or equal to the filament's length.

*Color*.—Considered a very pale green (RHS Yellow Green Group 151 D or RHS Yellow Green 154 C or RHS Yellow Green 154 D). The color evolves during the blooming, becoming more light (RHS Yellow Green 150 D) and sometimes very slightly pink (RHS Red Group 36D) at the end of the blooming.

*Ovary*.—

*Pubescence*.—Present.

*Height*.—Between 2.0 and 2.5 millimeters.

*Diameter*.—Between 1.0 and 1.5 millimeters.

*Color*.—Green (RHS Yellow Green 145 A or RHS Yellow Green 145 B).

*Stamen*.—Size compared to petals. — The size of stamen is smaller than the size of petals.

*Stigma*.—

*Position compared to anthers*.—The stigma is below the anthers.

*Diameter*.—Approximately 1.0 millimeter.

*Color*.—Yellow to pale green (RHS Yellow Green 154 C or RHS Yellow Green 154 D).

Fruit:

*Maturity when described*.—Firm in ripe conditions (shipping ripe).

*Date of first picking*.—Aug. 2, 2014.

*Date of last picking*.—The date of harvest varies slightly with the prevailing climatic conditions. The 'CRISPLOVA' variety has a medium to late date of picking, and a grouped maturity. The maturity is grouped within 9 days and the harvest is generally performed in two runs. Last known picking times carry on August $2^{nd}$ to Aug. 10, 2014, then on August $19^{th}$ to Aug. 27, 2015, then on August $27^{th}$ to Sep. 3, 2016 and then on August $23^{th}$ to Aug. 29, 2017.

*Size*.—

*Generally*.—Homogeneous in size. Considered large.

*Average cheek diameter*.—Approximately 70.0 to 76.0 millimeters.

*Average axial diameter*.—Approximately 62.0 to 65.0 millimeters.

*Typical weight*.—Generally about 190.0 to 220.0 grams. This characteristic is high dependent upon the prevailing cultural practices, and therefore is not particularly distinctive of the variety.

*Fruit form*.—

*Generally*.—Round. The fruit is generally uniform in symmetry, viewed from the suture's plane.

*Suture*.—

*Fruit suture*.—Wide-mouthed and slightly marked, extending from the base to the apex. No apparent callousing or stitching exists along the suture line. Not pointed.

*Color*.—The suture has generally a similar color to the whole fruit color, a luminous purple red (RHS Greyed Purple 187 A).

*Ventral surface*.—

*Form*.—Smooth.

*Apex*.—Non-prominent, small and generally slightly depressed.

*Base*.—Semi-flared, shallow.

*Stem cavity*.—Average depth of the stem cavity is about 12.0 to 14.0 millimeters. Average width is about 18.0 to 20.0 millimeters.

*Fruit skin*.—

*Thickness*.—Considered thick and strong, and the adherence of skin to flesh is strong to medium, depending on the fruit maturity.

*Texture*.—Fine pubescence.

*Taste*.—Semi-sweet and sugary.

*Tendency to crack*.—None observed.

*Color*.—

*Blush color*.—This blush color is an homogenous purple red (RHS Greyed Purple 187 A). The purple red blush covers approximately 95% of the fruit skin surface on an orange red background (RHS Greyed Orange 173 A) on approximately 5% of the fruit skin surface. The percentage of the blush on the fruit skin surface can vary, and is generally dependant upon the prevailing conditions under which the fruit was grown.

*Ground color*.—The ground color covers approximately 5% of the fruit skin surface, and is considered orange red (RHS Greyed Orange 173 A).

*Fruit stem*.—Medium in length, approximately 8.0 to 9.0 millimeters.

*Diameter*.—Approximately 4.0 to 5.0 millimeters.

*Color*.—Pale green (RHS Yellow Green 145 A).

*Flesh*.—

*Ripens*.—Very homogenously, slowly. The flesh has a long shelf life.

*Texture*.—Very firm, very dense, crunchy, melting, juicy at harvest maturity stage.

*Fibers*.—Not fibrous.

*Aroma*.—Pronounced.

*Eating quality*.—Considered very good, aromatic and with a high level of sugars.

*Flavor*.—Considered semi-sweet. The Brix is generally between 11.5 and 14.4.

*Juice*.—Very juicy at complete maturity.

*Brix*.—Generally 11.5 to 14.4 degrees. This characteristic varies slightly with the number of fruit per tree; prevailing cultural practices; and the surrounding climatic conditions.

*Flesh color*.—Orange yellow flesh (RHS Yellow 13 A to RHS Yellow 13 B) usually with a red pigmentation (RHS Orange Red N34 A) into the stone cavity and in a star shape around said cavity, on approximately 6.0 millimeters around the stone cavity.

Stone:

*Type*.—Clingstone, more or less adherent depending on the fruit maturity.

*Size*.—Considered medium to small for the variety. The stone size varies significantly depending upon the tree vigor, crop load and prevailing growing conditions.

*Length*.—Approximately 27.0 millimeters.

*Width*.—Approximately 18.0 millimeters.

*Diameter*.—Approximately 22.0 millimeters.

*Form*.—Elliptic.

*Base*.—Straight.

*Apex*.—

*Shape*.—The stone apex is short and pointed.

*Stone cavity*.—Considered small size, with an ovate-form and dimensions corresponding to the stone's dimensions.

*Stone surface*.—

*Surface texture*.—The pit is transversely furrowed on its entire surface. Furrows are more pronounced toward the apex. The stone is pitted toward the base. Relief is prominent generally and present basally.

*Ridges*.—The surface texture is generally characterized by more prominent ridges along the ventral edges and is more prominent at the apical tip.

*Ventral edge*.—

*Width*.—Considered small to medium, and having a depth of approximately 2.0 millimeters at mid-suture.

*Dorsal edge*.—

*Shape*.—Grooved.

*Stone color*.—The color of the dry stone is generally considered orange brown (RHS Greyed Orange 165 C to RHS Greyed Orange 165 D).

*Tendency to split*.—Splitting is very low or absent, depending on climatic conditions between blooming period and stone hardening.

*Kernel*.—

*Size*.—The kernel is considered medium.

*Length*.—Approximately 16.0 millimeters.

*Width*.—Approximately 10.0 millimeters.

*Thickness*.—Approximately 3.5 millimeters.

*Form*.—Considered flattened and elliptic.

*Pellicle*.—The pellicle of the kernel has a short pubescence.

*Color*.—The kernel skin is light orange-brown colored (RHS Greyed Orange 163 A). The almond, which is the seed of the kernel, is cream white (RHS White 155 D) and has a bitter taste. The kernel and its embryo are mature at the time of fruit maturity.

*Use*.—The subject variety 'CRISPLOVA' is considered to be a yellow peach tree of the medium season of maturity, and which produces fruits that are considered firm, attractively colored with a luminous purple red. Fruits have a semi-sweet taste and are excellent for uncooked consumption, crunchy or melting when at full maturity. Fruits have excellent gustative qualities. Due to their flesh quality, firmness and density, they can also be commercialized as $4^{th}$ range product (packed fruit or fruit in bags for example). And they are also useful for both local and very long distance shipping.

*Keeping quality*.—Remarkable. Fruit have a slow maturation and a long shelf life both on the tree after growth completion and after harvesting without alteration. After growth completion, fruits are preserved more than one week. After harvest, fruits are well preserved more than 4 weeks at 2.0 degree Celsius.

*Shipping quality*.—Considered very good. The fruit of the new yellow peach variety showed minimal bruising of the flesh or skin damage after being subjected to normal harvesting and packing procedures. Its resistance to handling during harvest and packing and its long shelf life without alteration after harvest easily permit 3 to 4 weeks-shipping at 2 degrees Celsius.

*Resistance to insects and disease*.—No particular susceptibilities were noted. The present variety is not very sensitive to powdery mildew, or conservation diseases and decay due to its thick and strong skin. More particularly, the leaves are considered moderately sensitive to powdery mildew (*Podosphaera leucotricha*), whereas the branches are considered not sensitive and the fruits are not very sensitive to this disease. The new variety is moderately sensitive to blight (*Puccinia*), not sensitive to black bean aphid (*Aphis fabae*), very sensitive to leafhopper (belonging to Cicadellidae family). The fruits are not sensitive to monilia (belonging to Sclerotiniaceae family).

Although the new variety of peach tree possesses the described characteristics when grown under the ecological conditions prevailing near Elne, Pyrénées-Orientales departement, France, it should be understood that variations of the usual magnitude and characteristics incident to changes in growing conditions, fertilization, pruning, pest control and horticultural management are to be expected.

I claim:

1. A new and distinct variety of yellow peach tree as illustrated and described, characterized by fruits with high eating quality and very long shelf life without alteration before and after harvesting, with a semi-sweet orange yellow flesh, with a red pigmentation into and around the stone cavity, the pigmentation having a star shape, and an attractive luminous and homogenous skin with a very high percentage of purple red blush on skin surface, on an orange red background.

* * * * *